(12) United States Patent
Ramey et al.

(10) Patent No.: US 8,383,056 B2
(45) Date of Patent: Feb. 26, 2013

(54) BLOOD GLUCOSE TEST INSTRUMENT KIT HAVING MODULAR COMPONENT PARTS

(75) Inventors: Blaine E. Ramey, Indianapolis, IN (US); Karl Werner, Wiesloch (DE); Richard W. Wilson, Fortville, IN (US); Christian Niesporek, Heidelberg (DE); Ralf Schmitz, Weinheim (DE); Peter Seelig, Frankfurt am Main (DE); Kai-Oliver Schwenker, Hassloch (DE); Ulrich Porsch, Weinheim (DE)

(73) Assignees: Roche Diagnostics Operations, Inc., Indianapolis, IN (US); Roche Diagnostics GmbH, Mannheim (DE)

( * ) Notice: Subject to any disclaimer, the term of this patent is extended or adjusted under 35 U.S.C. 154(b) by 98 days.

(21) Appl. No.: 12/905,485

(22) Filed: Oct. 15, 2010

(65) Prior Publication Data

US 2012/0094370 A1    Apr. 19, 2012

(51) Int. Cl.
    *G01N 33/00*    (2006.01)
(52) U.S. Cl. ........ 422/403; 422/401; 422/402; 422/68.1
(58) Field of Classification Search .................. 422/400, 422/401, 402, 403, 68.1
    See application file for complete search history.

(56) References Cited

U.S. PATENT DOCUMENTS

| | | | |
|---|---|---|---|
| 5,899,855 A * | 5/1999 | Brown | 600/301 |
| 6,050,940 A | 4/2000 | Braun et al. | |
| 7,768,408 B2 | 8/2010 | Reggiardo et al. | |
| 7,884,729 B2 | 2/2011 | Reggiardo et al. | |
| 2004/0199409 A1 | 10/2004 | Brown | |
| 2008/0300919 A1 | 12/2008 | Charlton et al. | |
| 2008/0301665 A1 | 12/2008 | Charlton et al. | |

FOREIGN PATENT DOCUMENTS

WO    WO2007/044599    4/2007

* cited by examiner

*Primary Examiner* — Sam P Siefke
(74) *Attorney, Agent, or Firm* — Harness, Dickey

(57) ABSTRACT

A blood glucose test instrument kit having modular component parts capable of being assembled into a plurality of different handheld blood glucose test instruments is disclosed. The kit comprises the combination of an interconnection platform adapted to connect to a collection of interoperable modules. The collection of interoperable modules including: a plurality of different measurement engine modules, at least one user interface module, at least one power supply module. A handheld blood glucose test instrument is assembled by the interconnection to the interconnection platform of at least one measurement engine module, at least one user interface module, and at least one power supply module. The inter-module communication among the modules connected thereto to achieve enhanced glucose test instrument reliability by effecting at least one reliability protocol selected from a group of reliability protocols.

13 Claims, 10 Drawing Sheets

BLOOD GLUCOSE TEST INSTRUMENT KIT HAVING MODULAR COMPONENT PARTS

FIELD

The present disclosure relates to a blood glucose test instrument kit having modular component parts capable of being assembled into a plurality of different handheld blood glucose test instruments.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Lab test results include HbA1C, cholesterol, triglycerides, and glucose tolerance. Healthcare professional recomendations include prescriptions, diets, test plans, and other information relating to the treatment of the patient.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

The design and manufacture of such handheld devices may occur in multiple jurisdictions and different standards may apply for different components of the handheld device. For instance, regulatory agencies in Europe and the United States may impose different standards for radio communications, medical devices, and other areas. Thus, there is a need for well-defined interfaces in the core of the handheld device that allow for modularity when integrating different components in the handheld device, such that the core functionality of the handheld device does not need to be modified depending on the components of the device.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In an aspect of the disclosure, a blood glucose test instrument kit has modular component parts capable of being assembled into a plurality of different handheld blood glucose test instruments. The kit comprises the combination of an interconnection platform adapted to fit within a portable housing that supports at least one display device and a collection of interoperable modules. Each of the modules has an interface adapted for connection to the interconnection platform, the collection of interoperable modules including a plurality of different measurement engine modules each having an input port to receive a blood sample carrier and producing blood test data, at least one user interface module adapted to couple to said display device and containing test logic for implementing at least one blood glucose test protocol, and at least one power supply module adapted, when connected to said interconnection platform, to provide operating power to other modules that are connected to said interconnection platform. A handheld blood glucose test instrument is assembled by the interconnection to the interconnection platform of at least one measurement engine module, at least one user interface module, and at least one power supply module. The interconnection platform providing inter-module communication among the modules connected thereto to achieve enhanced glucose test instrument reliability by effecting at least one reliability protocol selected from the group consisting of: (a) a connected measurement engine module from the plurality of measurement engine modules cooperating with a user interface module to instruct the user to remove the blood sample carrier when the measurement engine module detects the blood sample carrier is damaged; (b) the connected measurement engine module cooperating with the user interface module to instruct the user to insert a new code key, when the measurement engine module detects that a previously entered code key is incorrect; and (c) the connected measurement engine module cooperating with the user interface module to instruct the user to repeat an attempted blood glucose test when the connected measurement engine module detects that an insufficient amount of blood or control solution has been deposited on blood sample carrier.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

Corresponding reference numerals indicate corresponding parts throughout the several views of the drawings.

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
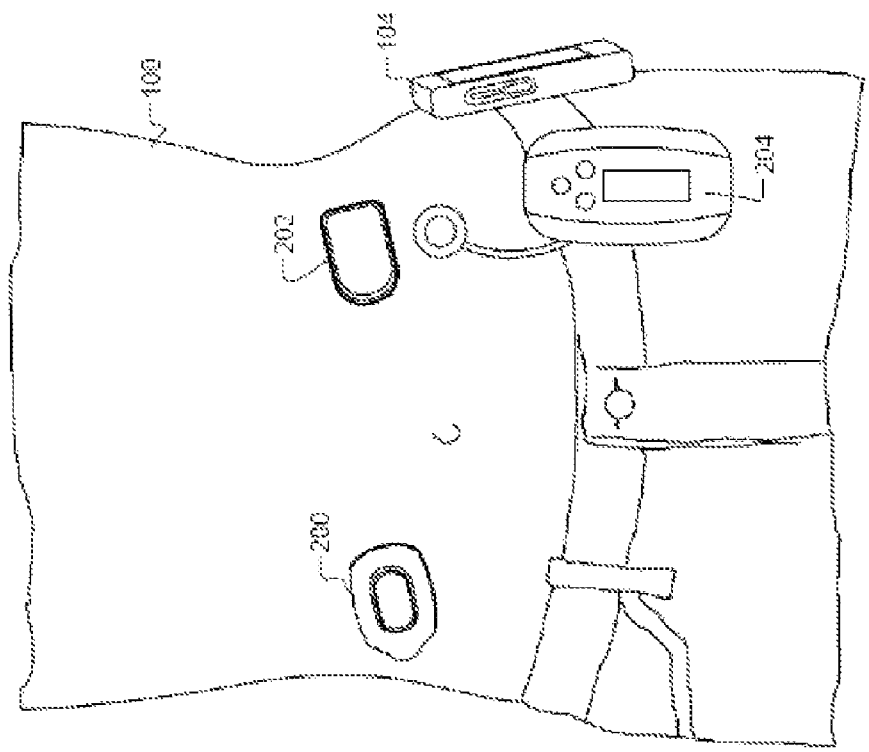
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetes, type 2 diabetes, and gestational diabetes and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
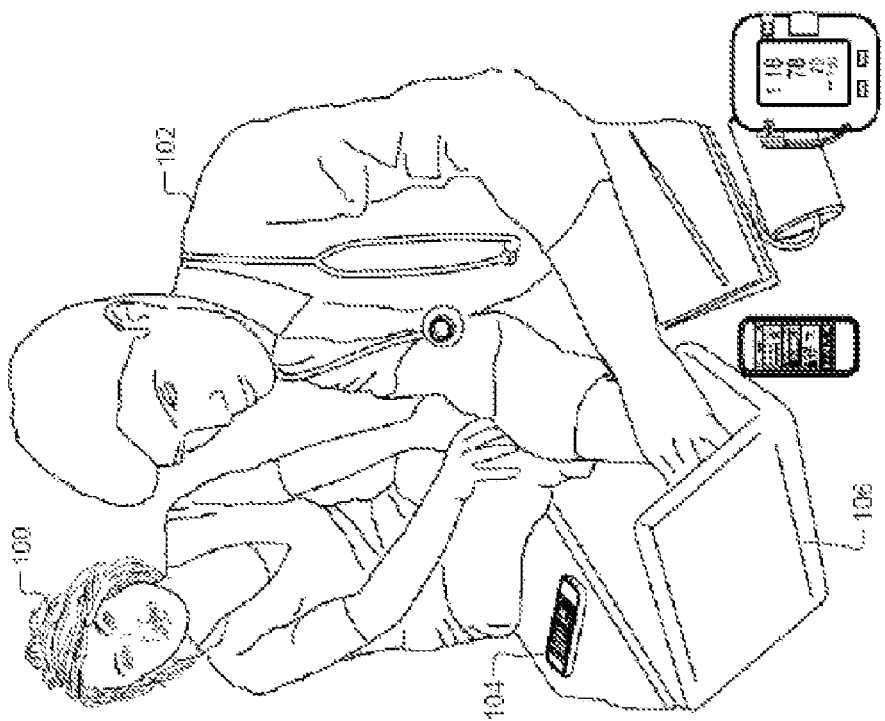
FIG. 2 shows a patient with a continuous glucose monitor (CGM), ambulatory durable insulin infusion pump, ambulatory non-durable insulin infusion pump, and diabetes manager.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the interstitial fluid of the patient 100 and communicates corresponding data to the handheld diabetes management device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM 200 from which glucose levels of the patient 100 are computed. The diabetes manager 104 transmits instructions to the insulin pump 202 or 204, which delivers insulin to the patient 100. Insulin can be delivered in the form of a bolus dose, which raises the amount of insulin delivered to the patient 100 by a predetermined amount. Additionally, insulin can be delivered in a scheduled manner in the form of a basal dose, which maintains a predetermined insulin dose to the patient 100.

Figure 3:
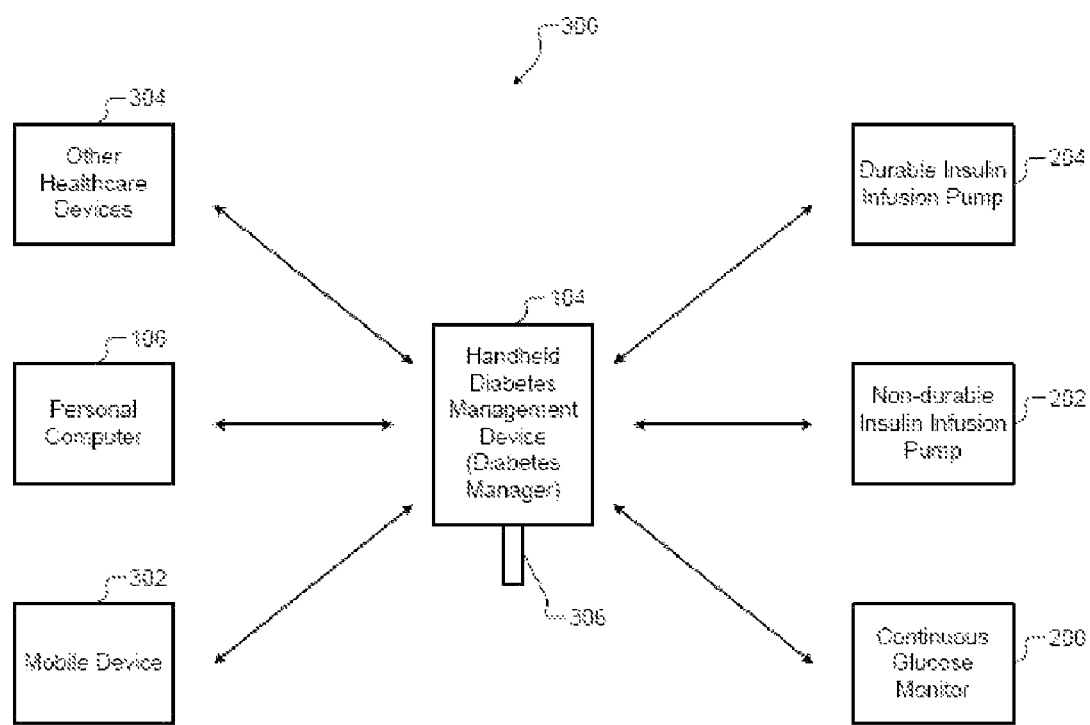
FIG. 3 shows a diabetes care system of systems used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as components of the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM 200). The CGM 200 continuously measures the glucose level of the patient 100. The CGM 200 periodically communicates the glucose level to the diabetes manager 104. The diabetes manager 104 and the CGM 200 communicate wirelessly using a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a PDA, or a pager. The diabetes manager 104 can send messages to an external network through the mobile device 302. The mobile device 302 can transmit messages to the external network based on requests received from the diabetes manager 104.

Figure 4:
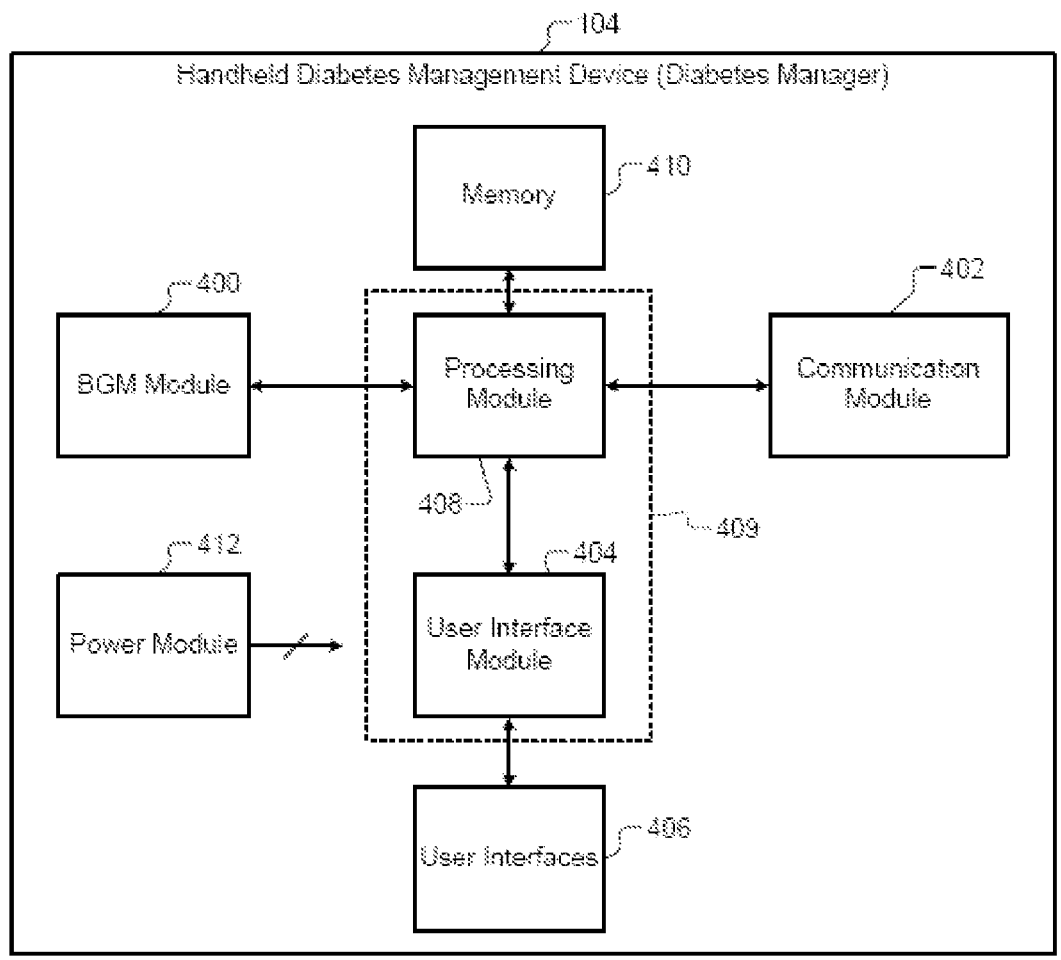
FIG. 4 shows a high level diagram of a diabetes care system-of-systems architecture.

Referring now to FIG. 4, the diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The nonvolatile memory may be a solid-state memory, such as flash memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Figure 5:
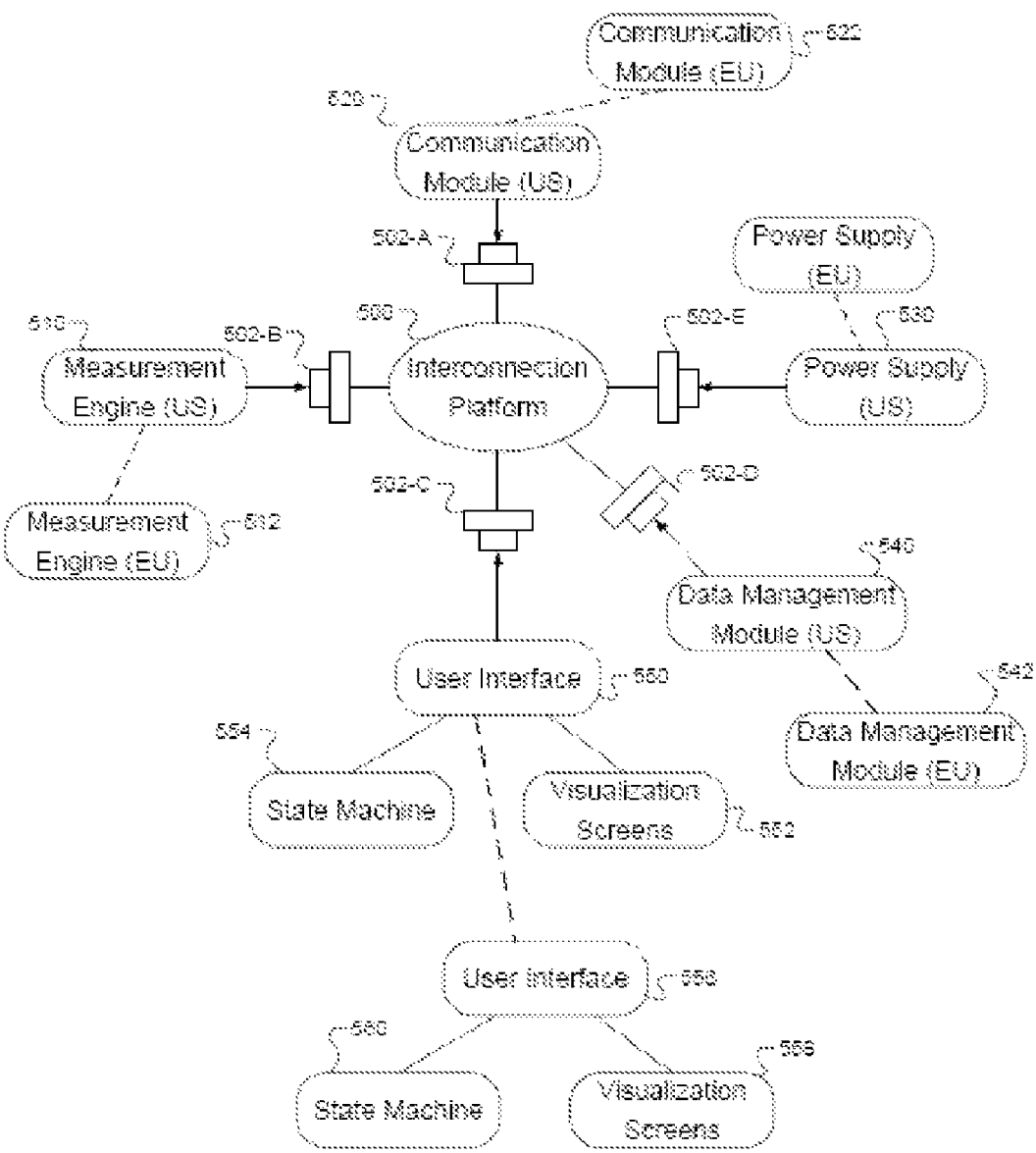
FIG. 5 shows a diagram of a modularized platform of a handheld diabetes manager.

FIG. 5 illustrates a platform that allows for modularization of the components of the diabetes manager. The processing module 408 (FIG. 4) includes an interconnection platform 500. The interconnection platform 500 is adapted to connect to a collection of interoperable modules, each of the modules having an interface adapted for connection to the interconnection platform 500, such that a first set of modules and a second set of modules are able to interface with the processing module 408. The inter connection platform is adapted to fit within a portable housing that supports at least one display device. The first set of modules includes a measurement engine 510, a communication module 520, a power supply 530, a data management module 540, and a user interface module 550, which are configured to electrically and physically couple to the interconnection platform 500 via an interface 502-A-502-E, e.g. pins adapted to couple to the modules. In this example, the modules that are connected to the interconnection platform 500 adhere to the standards, practices, and/or regulations of a first jurisdiction, e.g. the United States. The interface is standardized so as to receive a second set of components that comply with the standards, practices, and/or regulations of a second jurisdiction, e.g. the European Union. The second set of modules includes a second measurement engine 512, a second communication module 522, a second power supply 532, the data management module 540, and a second user interface module 556. The modularity afforded by the interconnection platform reduces development time and cost by providing a shared platform that can support different types of components, such as different types of measurement engines.

Due to practices of a region or country, some of the modules will have different designs or architectures. For example, regulations regarding radio communications in two different jurisdictions may require that the antennas on a communication module transmit at different frequencies. Thus, the first communication module 520 transmits at a first frequency or according to a first protocol and the second communication module 522 transmits at a second frequency or according to a second protocol. To accomplish modularity, however, the interconnection platform 500 is adapted to physically couple to both communication modules 520 and 522, via interface 502-A. Furthermore, the communication between the interconnection platform 500 and the communication modules 520 and 522, or any later developed communication modules, are standardized so as not to require modifications to be made to the physical interface 502-A of the interconnection platform 500.

Similarly, the interconnection platform 500 is adapted to connect to plurality of different measurement engine modules 510 and 512, each measurement engine module having an input port to receive a blood sample carrier and producing blood test data. For instance, the first measurement engine module 510 receives a test strip as a blood sample carrier and produces blood test data based on electrochemical sensing performed on the test strip. The second measurement engine module 512 receives a blood sample carrier and produces blood test data based on optical sensing performed on the blood sample carrier. In general, a measurement engine modules 510 or 512, is configured to receive, via the interface 502-B, a command from the interconnection platform 500 to perform a blood glucose test. The measurement engine modules 510 and 512 are configured to respond to the interconnection platform 500 with, for example, a status of the blood glucose test, the results of the blood glucose test, or feedback such as: what code key is used, when the measurement engine is ready for a blood strip carrier to be inserted, when a sample should be applied to the blood sample carrier. The process of a blood glucose test is described in greater detail below.

The interconnection platform 500 is further adapted to connect to at least one user interface module 550 adapted to couple to the display device and containing test logic for implementing at least one structured blood glucose test protocol. In this embodiment, the user interface module includes a visualization module 552 that performs the display functionality of the user interface module and a state machine 554, which contains the test logic for implementing the at least one structured blood glucose test protocol. The visualization module 552 provides the screens that can be displayed to a user during a blood glucose test for the measurement engine module 510. The state machine implements the test logic for implementing the blood glucose test protocol for the first measurement engine module 510. When the second measurement engine module 512 is used in the diabetes manager, however, the second user interface module 556 can be connected to interface 502-C the interconnection platform 500, as a different blood glucose test protocol may be required, which would require a different state machine 558 and a different visualization module 552.

The interconnection platform 500 is further adapted to connect to at least one data management module 540 for storing data based upon said blood test data. The data management module 540 receives the blood test data and stores the blood test data in a data store integrated into the diabetes manager. The data management module 540 is connected to the interconnection platform 500 by interface 502-D. It is appreciated that communication between the data management module 540 and the interconnection platform is achieved via interface 502-D.

The interconnection platform 500 is further adapted to connect to connect to at least one power supply module 530 via interface 502-E. The power supply module 530 or 532 is adapted, when connected to the interconnection platform, to provide operating power to other modules that are connected to said interconnection platform. It is noted, that based on the type of measurement engine module 510 or 512, the amount of power that is necessary to power the measurement engine module 510 or 512 can differ. Thus, if the first measurement engine module 510 is used, then the first power supply module 530 is connected to the interconnection platform 500. If the second measurement engine module 512 is used, then the second power supply module 532 is connected to the interconnection platform 500.

As mentioned, the interfaces 502-A-502-E are comprised of a series of interface pins. The pins communicate signals sent from one of the modules to the interconnection platform 500 and from the interconnection platform 500 to the intended module. Exemplary signals that are communicated to the measurement engine module 510 through interface 502-B include a power signal providing power to the interconnection platform 500, a reset signal requesting that a module reset, an event signal indicating that an event of interest has occurred, a ready signal indicating that measurement engine module 510 is ready to respond to requests, and an event interrupt signal requesting attention from the processing module 408. It is appreciated that similar signals may be transmitted via interfaces 502-A, 502-C, 502-D, and 502-E.

A handheld blood glucose test instrument is assembled by the interconnection to the interconnection platform 500 of at least one measurement engine module 510, at least one user interface module 550, and at least one power supply 530 module and further by the optional interconnection to the interconnection platform of at least one data management module 540, and by the optional interconnection to the interconnection platform 500 of at least one communication module 520. It is appreciated that the handheld glucose test instrument is integrated into the diabetes manager.

Once the various components are interconnected, the handheld blood glucose test instrument is realized. A patient can interact with the user interface module 550 and the measurement engine module 510 to obtain a blood glucose test measurement. As mentioned, the user interface module 550 has a state machine 554 and visualization screens 552 associated therewith. The state machine 554 maintains the state of the measurement engine 510, such that when a patient's blood glucose is to be tested, the state machine 554 provides test logic for implementing at least one blood glucose test protocol.

Figure 6:
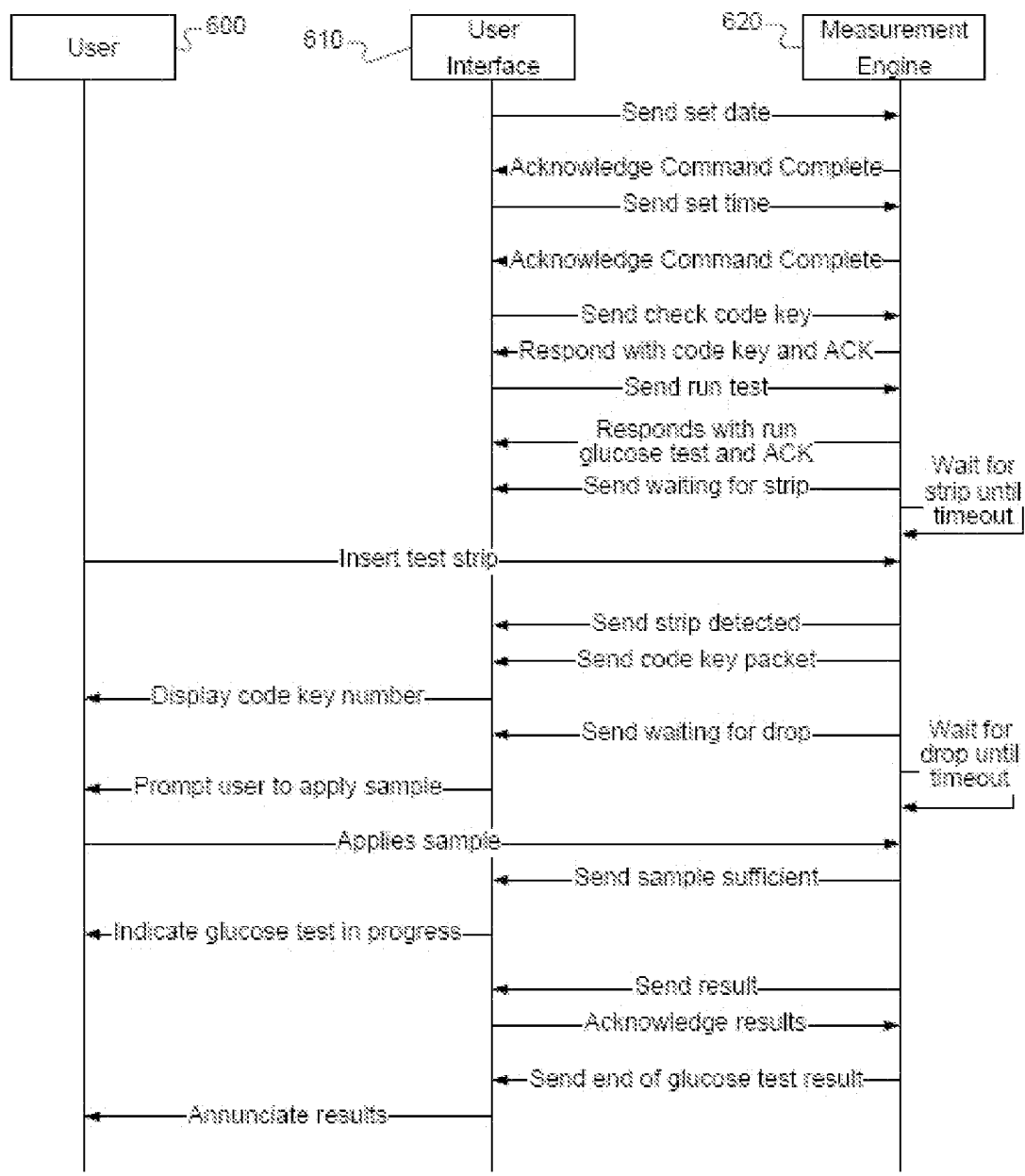
FIG. 6 shows a sequence diagram of a blood glucose test performed according to a blood glucose test protocol.

FIG. 6 illustrates a sequence diagram of a blood glucose test being performed according to an exemplary test protocol. The interconnection platform 610 facilitates interaction between a patient 600 and a measurement engine module 620. In this example, the measurement engine module 620 utilizes test strips as the blood sample carrier. Initially, upon removing the measurement engine module 620 from an OFF state or a SLEEP state, the interconnection platform 610 will transmit a set date command to the measurement engine module 620, thereby instructing the measurement engine module 620 to set a valid date. The measurement engine module 620 sets its internal date and responds with an acknowledgment (ACK) indicating that the valid date has been set. In general, the measurement engine module 620 utilizes ACKs to inform the interconnection platform 610 that a command was received and performed. Upon receiving the ACK from the measurement engine module 620, the interconnection platform 610 sends a request to set the time. The measurement engine module 620 sets a valid time and transmits an ACK to the interconnection platform 210. At this juncture, a valid date and time have been sent and the management engine can begin preparing to execute a blood glucose test.

Before the blood glucose test can be executed, the interconnection platform 610 executes a series of commands to verify that a code key provided to the measurement engine module 620 is valid and available. The code key information is downloaded to the measurement engine module 620 prior to the execution of the blood glucose test. A code key is used by the measurement engine 620 to calibrate the test strips to the measurement engine module 620. The code key can be embedded on a chip that is inserted into a port of the measurement engine module 620 or can be entered manually by the user, via the user interface module. The interconnection platform 610 sends a request to the measurement engine module 620 to determine if a code key has been provided to the measurement engine module 620 and, if so, whether the code key is valid. If the code key is valid, the measurement engine module 620 responds with the code key status and an ACK. If no valid code is available or found, the measurement engine module 620 will send a negative acknowledgement (NACK) to the interconnection platform, indicating an error. Recovery from test failures is discussed in greater detail below.

Once the ACK indicating a valid code key is received, the interconnection platform 610 initiates a blood glucose test by sending a run test command to the measurement engine module 630. The measurement engine module 620 responds with an ACK once the measurement engine module 620 is ready to execute a glucose test. The measurement engine module 620 then sends a signal indicating that it is waiting for a strip to be inserted into the measurement engine module 620. The measurement engine module 620 then waits for the user to enter a strip. The interconnection platform 610 then displays, via the user interface module, a screen to the user prompting the user to insert a strip. If a strip is not inserted within a timeout period, the blood glucose test is aborted.

Once a strip is detected in the measurement engine module 620, the measurement engine module 620 transmits a signal indicating that a strip has been detected to the interconnection platform 610. The signal can be a bit string of predetermined length that indicates the current status of the strip, but may not indicate whether the strip is fully or correctly inserted. It is noted that the measurement engine module 620 can perform a more exhaustive strip insertion confirmation, which indicates that the strip is present but not fully inserted. The measurement engine module 620 also transmits a code key packet indicating a code key lot number of fixed length. The interconnection platform 610 then displays, via the user interface module, a screen to the user indicating the code key number to the user, via the display device. In some embodiments, the last three digits of the code key lot number are displayed to the user for user confirmation of the correct code key.

Once the measurement engine module 620 confirms that the strip is fully inserted, the measurement engine module 620 transmits to the interconnection platform 610, a signal indicating that the code key is OK and a signal indicating that the measurement engine module 620 is waiting for a sample, e.g. a drop of blood. The interconnection platform 610 then displays, via the user interface module, a screen to the user 600 prompting the user 600 to apply a sample to the test strip. The measurement engine module 620 waits for the sample. If a sample is received before a timeout period has lapsed and the amount is sufficient to determine a result, the measurement engine module 620 sends a signal indicating that the sample is sufficient to the interconnection platform 610. Upon receiving an indication that the sample was sufficient, the user interface module displays a screen to the user 600 indicating that the glucose test is in progress.

Once a result is determined by the measurement engine module 620, the measurement engine module 620 sends the result to the interconnection platform 610. The interconnection platform 610 then sends an ACK to the measurement engine module 620. The measurement engine module 620 then sends an end of test signal to the interconnection platform 610. The user interface module then displays the result to the user 600.

It is noted that if at any time an error occurs at the measurement engine module 620, the measurement engine module 620 will send a NACK with an error code to the interconnection platform 610.

It is further noted that the foregoing sequence is exemplary and pertains to a measurement engine module 620 that utilizes test strips. It is appreciated that the interconnection platform 610 is configured to execute variations of the above described sequence when connected to different measurement engine modules, e.g. a measurement engine module that performs optical sensing. As the exact sequence of events will vary from measurement engine module to measurement engine module, the test logic for implementing the blood glucose test will change. Thus, when a different measurement engine module is connected to the interconnection platform 610, a new user interface module containing different visualization screens and a different state machine providing the test logic will be connected to the interconnection platform as well. The set of commands and signals, however, will remain the same, thereby promoting modularity. Meaning that the interconnection platform 610 will transmit these signals to a measurement engine module, independent on the type of measurement engine module, and the measurement engine module will be configured to interpret the commands and signals. For instance, commands such as set date, set time, and run test should be understood by any measurement engine module. Thus, the configuration of the interconnection platform 610 will not need to be significantly altered, if at all, to support different measurement engine modules.

Figure 7:
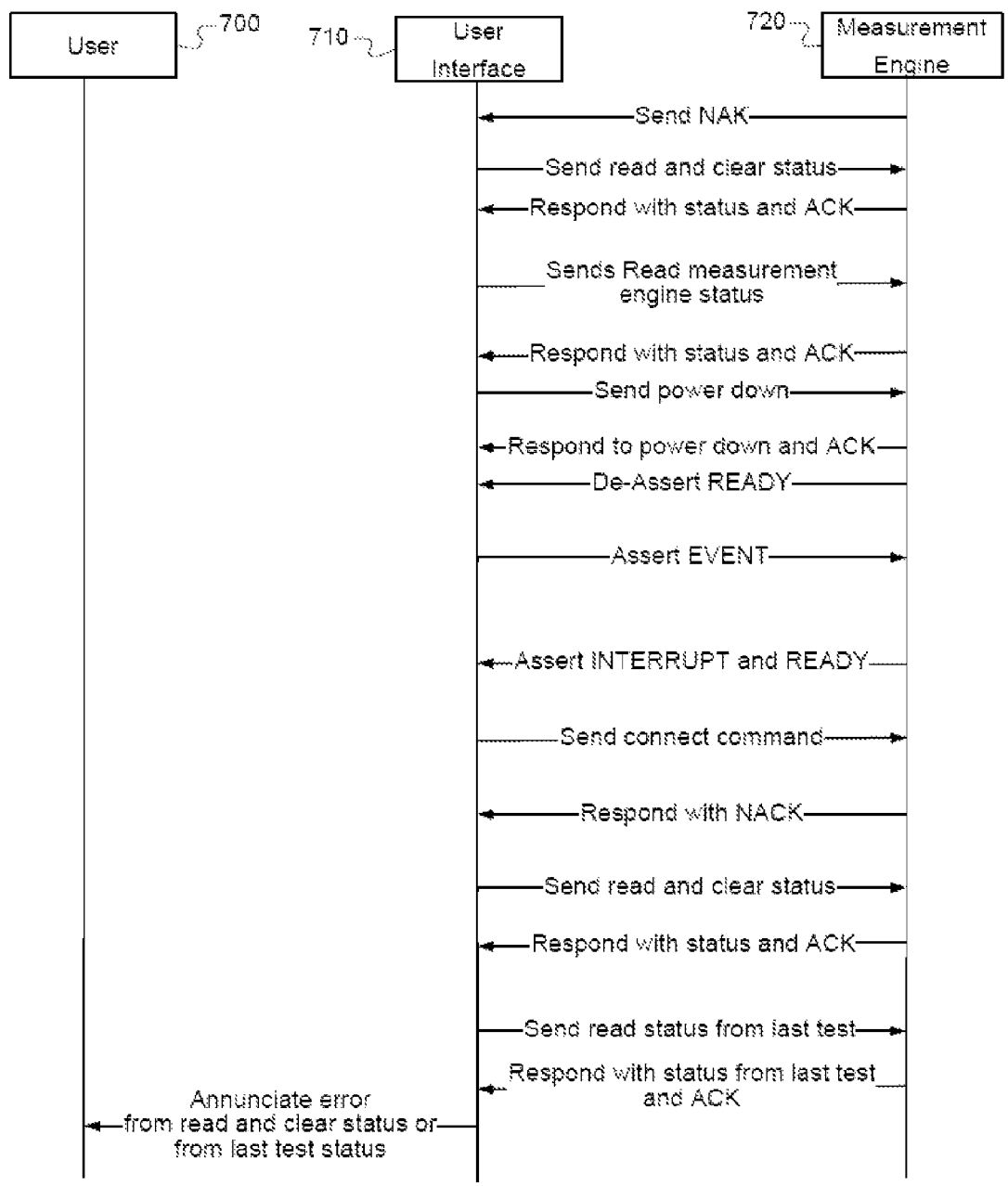
FIG. 7 shows a sequence diagram of a recovery from a blood glucose test failure according to a blood glucose test protocol.

FIG. 7 is a sequence diagram of a recovery from a glucose test failure. The following sequence occurs when the measurement engine module 720 has received a request to run the test but an error condition has been detected during the execution of a blood glucose test. Once an error has been detected, the measurement engine module 720 sends a NACK to the interconnection platform 710. The interconnection platform 710 responds with a read and clear status command to the measurement engine module 720. The read and clear status command allows the interconnection platform 710 read a serial status register of the measurement engine module 720. Once the command initiates, the serial status register is cleared. The measurement engine module 720 returns the status and resets the status of the measurement engine module 720, and returns an ACK to the interconnection platform 710. The interconnection platform can communicate the received status to the data management module for archiving in a database that records the operational status of the modules of the diabetes manager.

The interconnection platform 710 then sends a read measurement engine status command. The read measurement engine status command allows the host to determine what events and states the measurement engine module 720 has detected. The measurement engine module 720 returns the status of the measurement engine module 720 in a fixed length bit string, wherein predetermined bits are flags indicating status of the measurement engine module 720. For instance, the flags can indicate whether a strip has been removed, whether a strip is present, whether the temperature of the measurement engine module 720 is in a warning condition or in an error condition, whether the power supply module is in a warning condition or error condition, or whether there has been a clock error. If the status indicates that the strip has not been removed, then the interconnection platform waits until the strip is removed before initiating a new test.

If the interconnection platform 710 does not receive a proper response to a request for the status, the interconnection platform 710 sends a power down signal to the measurement engine module 720. The measurement engine module 720 powers down to a sleep mode and responds to the interconnection platform with an ACK. Once powered down, the measurement engine module 720 de-asserts a ready signal that was asserted during the testing phase. The interconnection platform 710 waits a predetermined amount of time, e.g. 10 ms, and then asserts an event signal to the measurement engine module 720, thereby removing the measurement engine module 720 from the sleep mode. In response, the measurement engine module 720 asserts an event interrupt signal and a ready signal, thereby indicating that the measurement engine module 720 has removed itself from the sleep mode.

In response to the ready signal, the interconnection platform 710 sends a connect command to the measurement engine module 720. If the serial status register has not been cleared, the measurement engine module 720 responds with a NACK. If, however, the serial status register has been cleared, the interconnection platform 710 responds with an ACK. Assuming a NACK is received by the interconnection platform 710, the interconnection platform 710 sends a read and clear status command to the measurement engine module 720. The measurement engine module 720 clears the serial status register and responds with the status and an ACK.

Once the ACK is received, the interconnection platform 710 sends a read status from last test command. The read status from last test command allows the interconnection platform 710 to read the last test result stored in a memory of the measurement engine module 720. The last result will include a bG value, a time, a date, and result flags. The result flags is a fixed length bit string having flags indicating, inter alia, whether the bG value is less than a first reliability threshold, i.e. too low to be trusted, whether the bG value is greater than a second reliability threshold, i.e. too high to be trusted, and whether the measurement engine module 720 issued a temperature warning.

Upon receiving the read status from last test command, the measurement engine module 720 responds with the status of the last test and an ACK. Upon receiving the read status from last test command, the interconnection platform 710 displays at least one of the read and clear status command result and the read status from last test command to the user 700, via the user interface module.

The foregoing sequence is exemplary and pertains to a measurement engine module 720 that utilizes test strips. It is appreciated that the interconnection platform 710 is configured to execute a variation of this sequence when connected to different measurement engine modules, e.g. a measurement engine module that performs optical sensing. As the exact sequence of events will vary from measurement engine module to measurement engine module, the test logic for implementing the blood glucose test will change. Thus, when a different measurement engine module is connected to the interconnection platform 710, a new user interface module containing different visualization screens and a different state machine providing the test logic will be connected to the interconnection platform as well. The set of commands and signals, however, will remain the same, thereby promoting modularity. The interconnection platform 710 will transmit these signals to a measurement engine module, independent on the type of measurement engine module, and the measurement engine module will be configured to interpret the commands and signals. For instance, commands such as read and clear status, read measurement engine status, and connect, as well as signals such as, EVENT and READY, will be understood by different measurement engines. Thus, the configuration of the interconnection platform 610 will not be need to be significantly altered, if at all, to support different measurement engine modules.

It is noted that the interconnection platform 500 (FIG. 5) provides inter-module communication among the modules connected thereto to achieve enhanced glucose test instrument reliability by effecting at least one reliability protocol. The reliability protocols are defined by a set of actions that the modules can perform in combination with one another to increase the reliability of the blood glucose test instrument.

Figure 8:
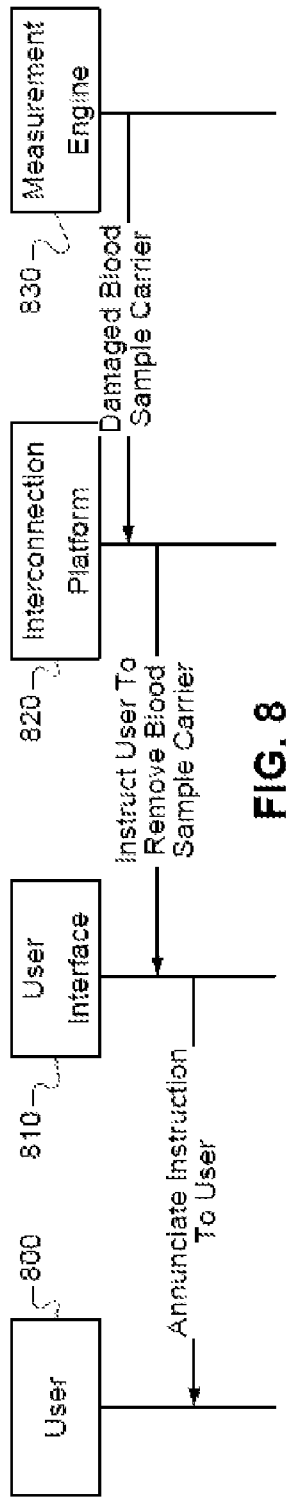
FIG. 8 shows a sequence diagram of the effecting of a first reliability protocol.

FIG. 8 illustrates an exemplary reliability protocol that ensures that the patient does not attempt to execute a blood glucose test with a damaged blood sample carrier. In this protocol a connected measurement engine module 830 cooperates with the user interface module 810 to instruct the user 800 to remove the blood sample carrier when the measurement engine module detects the blood sample carrier is damaged. As discussed above, the measurement engine module 830 will send a status thereof to the interconnection platform 820. Upon receiving a status indicating that the blood sample carrier, e.g. the test strip, is damaged, the interconnection platform 820 instructs the user interface module to display an instruction to the user to remove the damaged blood sample carrier. The user interface module 810 presents the instruction to the user 800 visually, e.g. displaying the instruction on a screen, and/or audibly, e.g. outputting the instruction on the speaker.

Figure 9:
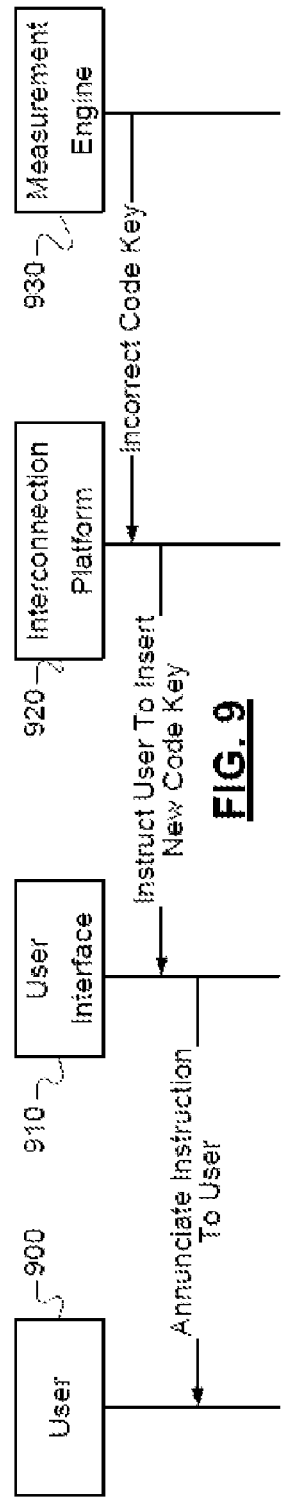
FIG. 9 shows a sequence diagram of the effecting of a second reliability protocol.

FIG. 9 illustrates an exemplary reliability protocol that ensures that the user has provided the proper code key. According to this protocol, the connected measurement engine module 930 cooperates with the user interface module 910 to instruct the user to insert a new code key when the measurement engine module 930 detects that a previously entered code key is incorrect. As mentioned, the measurement engine module 930 reports whether the correct code key has been entered by the user. Upon detecting that the code key is incorrect, the measurement engine module 930 will notify the interconnection platform 920 that the code key is incorrect. The interconnection platform then transmits a command to the user interface module 910 to instruct the user 900 to enter a new code key. The user interface module 910 then presents the instruction to the user 900 visually and/or audibly.

Figure 10:
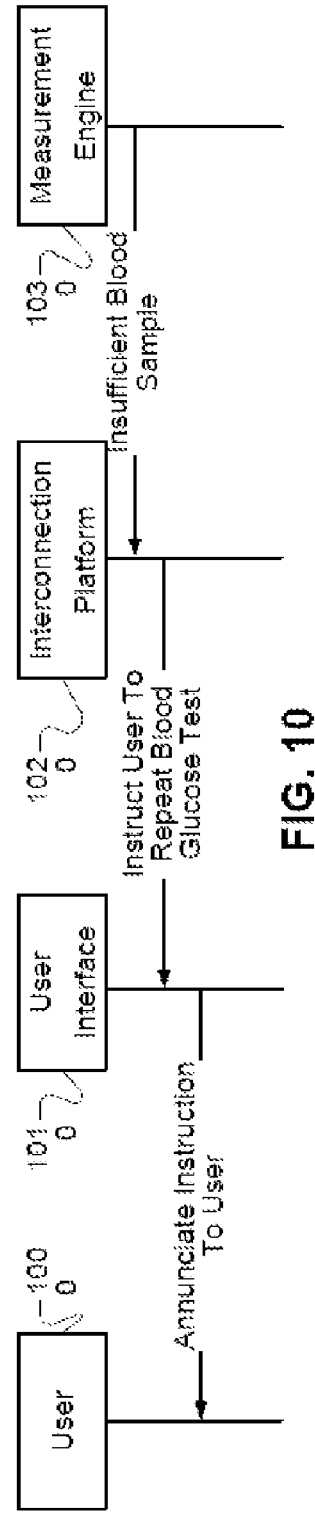
FIG. 10 shows a sequence diagram of the effecting of a third reliability protocol.

FIG. 10 illustrates an exemplary reliability protocol that ensures that the user has provided a sufficient blood sample and control sample. According to this protocol, the connected measurement engine module 1030 cooperates with the user interface module 1010 to instruct the user to repeat an attempted blood glucose test when the connected measurement engine 1030 detects that an insufficient amount of blood or control solution has been deposited on blood sample carrier. Upon detecting an insufficient amount of blood on the blood sample carrier or an insufficient amount of control solution, the blood measurement module 1030 will notify the interconnection platform 1020 of the insufficient sample. The interconnection platform 1020 then commands the user interface module 1010 to instruct the user 1000 to repeat the blood glucose test. The user interface module 1010 then presents the instruction to the user 1000 visually and/or audibly.

Figure 11:
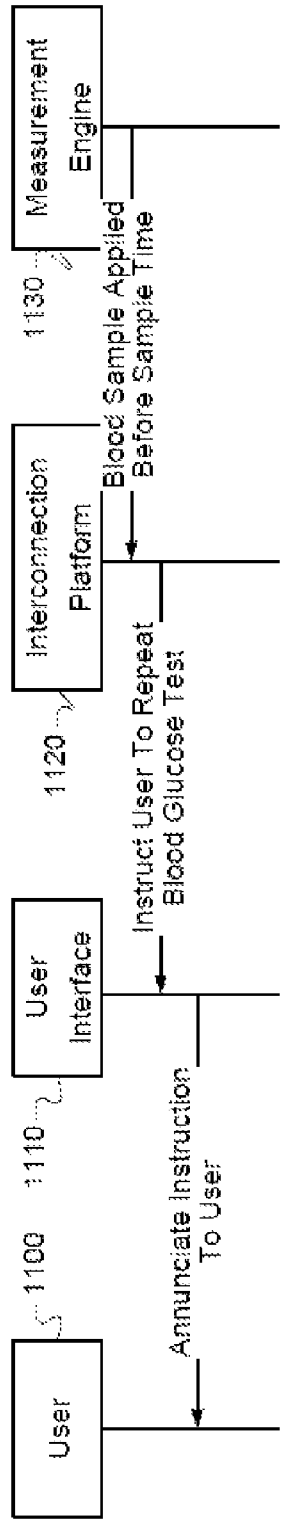
FIG. 11 shows a sequence diagram of the effecting of a fourth reliability protocol.

FIG. 11 illustrates an exemplary reliability protocol that ensures that the user 1100 follows the procedures indicated in the glucose test protocol. According to this protocol, the connected measurement engine cooperates with the user interface module to instruct the user to repeat an attempted blood glucose test when the connected measurement engine detects that the user failed to adhere to a sequence defined in the blood glucose test protocol. In the example of FIG. 11, the user 1100 applies a drop of blood to the blood sample carrier before the measurement engine module 1130 has transmitted a ready for blood sample signal to the interconnection platform 1120. Once this occurs, the measurement engine module 1130 notifies the interconnection platform 1120 of the failure to adhere to the sequence defined in the test protocol. The interconnection platform 1120 then commands the user interface module 1110 to instruct the user 1100 to repeat the blood glucose test. The user interface module 1110 then presents the instruction to the user 1100 visually and/or audibly.

Figure 12:
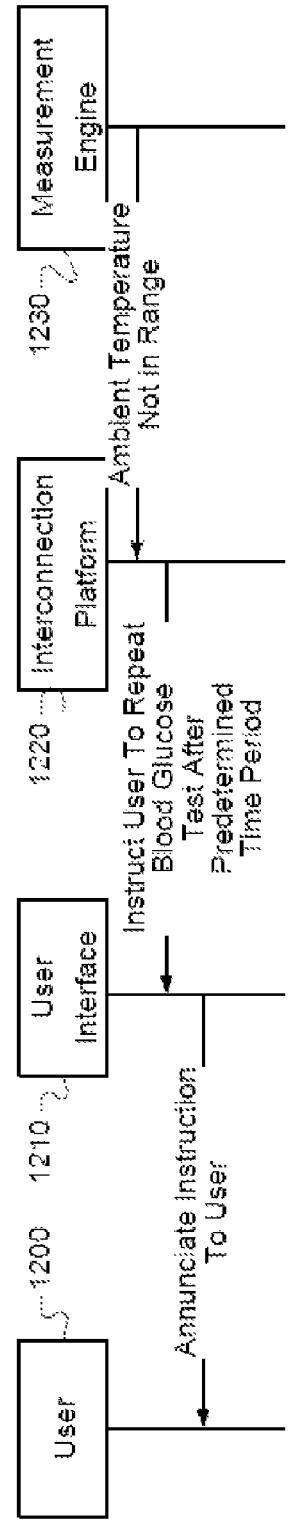
FIG. 12 shows a sequence diagram of the effecting of a fifth reliability protocol.

FIG. 12 illustrates an exemplary reliability protocol that ensures that the blood glucose test is being conducted in an appropriate temperature. It is appreciated that a blood glucose test should be performed in an optimal temperature range. Thus, the measurement engine module 1230, in some embodiments, will have a temperature sensor, e.g. a thermistor, embedded therein. According to this protocol, the connected measurement engine module 1230 cooperates with the user interface module 1210 to instruct the user to repeat an attempted blood glucose test when the connected measurement engine module 1230 detects that an ambient temperature outside of the connected measurement engine module 1230 is not within a predefined temperature range. When the measurement engine module 1230 detects that the ambient temperature is either less than a first threshold, e.g. 6 C, or greater than a second threshold, e.g. 44 C, the measurement engine module 1230 will notify the interconnection platform 1220 of the error condition. The interconnection platform 1220 then command the user interface module 1210 to instruct the user 1200 to wait a predetermined amount of time, e.g. 5 minutes, and to repeat the blood glucose test. The user interface module 1210 then presents the instruction to the user 1200 visually and/or audibly.

Figure 13:
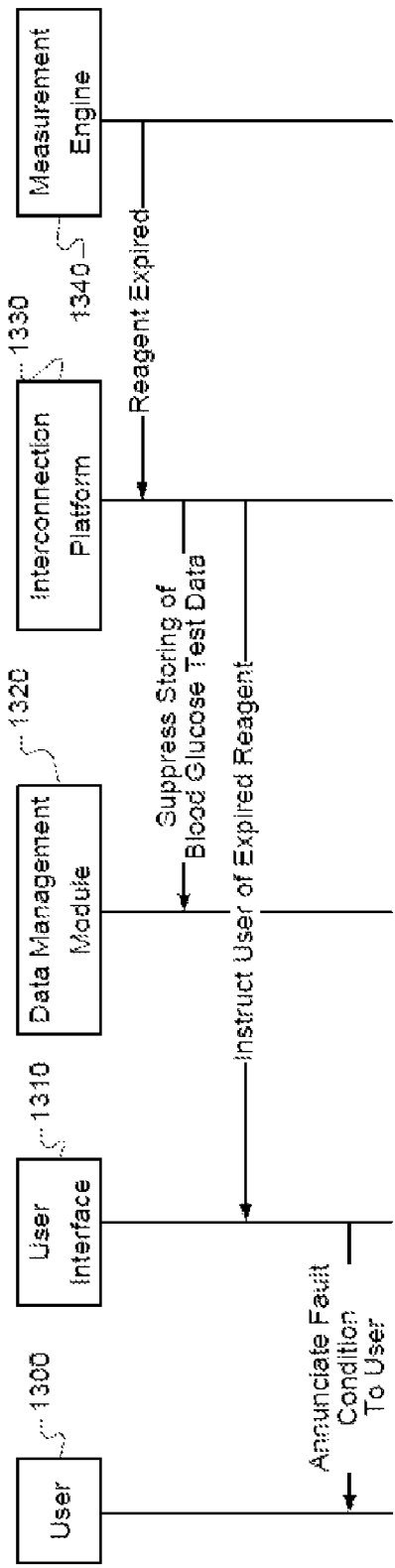
FIG. 13 shows a sequence diagram of the effecting of a sixth reliability protocol.

FIG. 13 illustrates an exemplary reliability protocol that ensures that the blood glucose test was conducted with valid test strips. According to this protocol, the user interface module 1310 cooperates with the connected measurement engine module 1340 and the data management module 1320 to suppress generation of blood test data when an expiry date of a reagent used in the blood sample carrier has passed and to communicate a fault condition message to the user. When the measurement engine module 1340 detects that the expiration date of a strip has passed, i.e. the reagent found on the test strip has expired, the measurement engine module 1340 will notify the interconnection platform 1330 that a test was performed using an expired test strip. For example, the measurement engine module 1340 can be configured to compare the date set at the beginning of the blood glucose test, as discussed with respect to FIG. 6, and a expiration date contained in the key code or entered by the user. If the set date is passed the expiration date, then the measurement engine module 1340 notifies the interconnection platform 1330. The interconnection platform 1330 will instruct the data management module 1320 to suppress storing of the blood glucose test data and will command the user interface module 1310 to notify the user 1300 of the expired test strips. The user interface module 1310 then presents the notification to the user 1300 visually and/or audibly.

Figure 14:
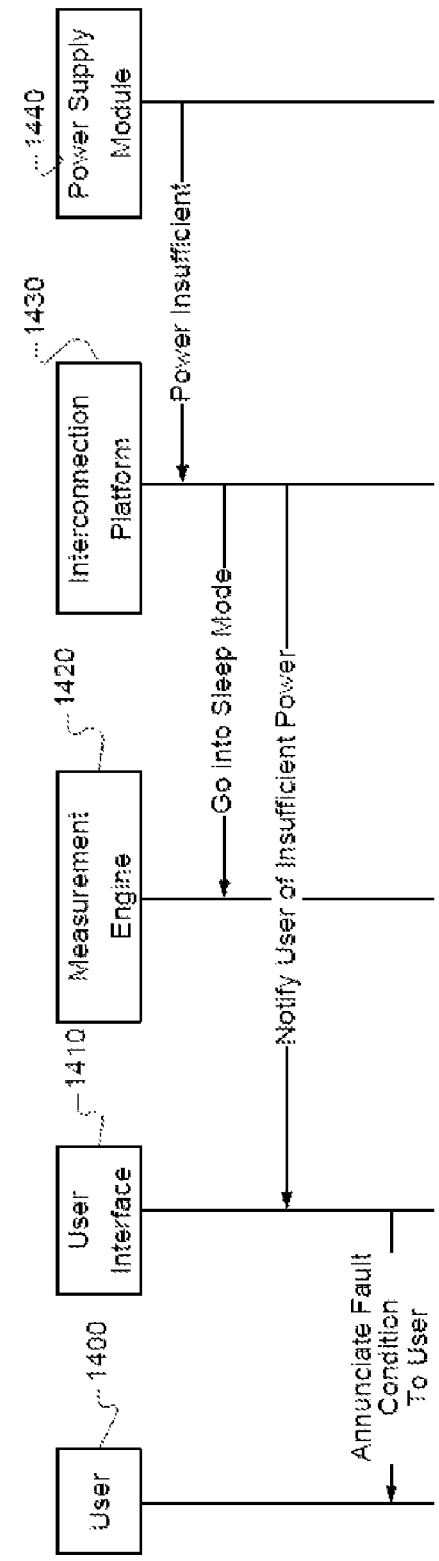
FIG. 14 shows a sequence diagram of the effecting of a seventh reliability protocol.

FIG. 14 illustrates an exemplary reliability protocol that ensures that the power supply module 1440 has sufficient power to power the measurement engine module 1420. According to this protocol, the power supply module 1440 cooperates with the connected measurement engine module 1420 and the user interface module 1410 to communicate a fault condition message to the user when power supply module resources are insufficient to reliably produce blood test data. When the power supply module 1440 determines that a battery or other power source has insufficient energy left to power the measurement engine module 1420, the power supply module 1440 notifies the interconnection platform 1430 that the power supply module resources are insufficient. The interconnection platform 1430 then commands the measurement engine module 1420 to enter a sleep mode. The interconnection platform 1430 will also command the user interface module 1410 to notify the user 1400 that the power supply resources are insufficient to power the measurement engine 1420. The user interface module 1310 then presents the notification to the user 1300 visually and/or audibly.

Figure 15:
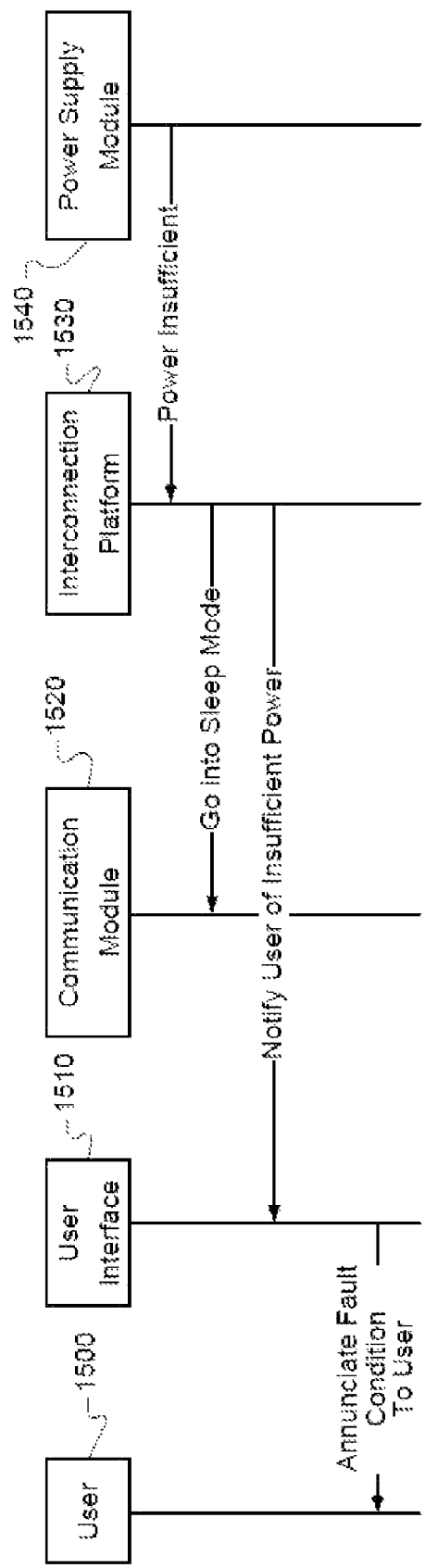
FIG. 15 shows a sequence diagram of the effecting of an eight reliability protocol.

FIG. 15 illustrates an exemplary reliability protocol that ensures that the power supply module 1540 has sufficient power to power the communication module 1520. According to this protocol, the power supply module 1540 cooperates with the communication module 1520 and the user interface module 1510 to communicate a fault condition message to the user interface module 1510 when power supply module resources are insufficient to reliably communicate with a separate therapy system. When the power supply module 1540 determines that a battery or other power resource has insufficient energy left to power the communication module 1520, the power supply module 1540 notifies the interconnection platform 1530 that the power supply module resources are insufficient. The interconnection platform 1530 then commands the communication module 1520 to enter a sleep mode. The interconnection platform 1530 will also command the user interface module 1510 to notify the user 1500 that the power supply resources are insufficient to power the communication module 1520. The user interface module 1310 then presents the notification to the user 1300 visually and/or audibly.

In an aspect of the disclosure, a blood glucose test instrument kit having modular component parts capable of being assembled into a plurality of different handheld blood glucose test instruments has been described. The kit includes the combination of an interconnection platform adapted to fit within a portable housing that supports at least one display device, and a collection of interoperable modules. Each of the modules having an interface adapted for connection to the interconnection platform. The collection of interoperable modules includes a plurality of different measurement engine modules each having an input port to receive a blood sample carrier and producing blood test data, at least one user interface module adapted to couple to the display device and containing test logic for implementing at least one blood glucose test protocol, at least one power supply module adapted, when connected to the interconnection platform, to provide operating power to other modules that are connected to the interconnection platform. A handheld blood glucose test instrument is assembled by the interconnection to the interconnection platform of at least one measurement engine module, at least one user interface module, and at least one power supply module. The interconnection platform provides inter-module communication among the modules connected thereto to achieve enhanced glucose test instrument reliability by effecting at least one reliability protocol selected from the group consisting of (a) a connected measurement engine module from the plurality of measurement engine modules cooperating with a user interface module to instruct the user to remove the blood sample carrier when the measurement engine module detects the blood sample carrier is damaged; (b) the connected measurement engine module cooperating with the user interface module to instruct the user to insert a new code key, when the measurement engine module detects that a previously entered code key is incorrect; and (c) the connected measurement engine module cooperating with the user interface module to instruct the user to repeat an attempted blood glucose test when the connected measurement engine module detects that an insufficient amount of blood or control solution has been deposited was deposited on blood sample carrier.

In another feature of the disclosure, the group of reliability protocols further includes the connected measurement engine module cooperating with the user interface module to instruct the user to repeat an attempted blood glucose test when the connected measurement engine module detects that the user failed to adhere to a sequence defined in the blood glucose test protocol.

In another feature of the disclosure, the group of reliability protocols further includes the connected measurement engine module cooperating with the user interface module to instruct the user to repeat an attempted blood glucose test when the connected measurement engine module detects that an ambient temperature outside of the connected measurement engine module is not within a predefined temperature.

In another feature of the disclosure, the collection of modules further include at least one data management module for storing data based upon the blood test data. The handheld blood glucose test instrument is further assembled by the interconnection to the interconnection platform of the data management module.

In another feature of the disclosure, the group of reliability protocols further includes the user interface module cooperating with the connected measurement engine module and the data management module to suppress generation of blood test data when an expiry date of a reagent used in the blood sample carrier has been passed and to communicate a fault condition message to the user.

In another feature of the disclosure, group of reliability protocols further includes the user interface module cooperating with the data management module and the measurement engine module to suppress the storing of data based upon the blood test data when the measurement engine module detects a fault condition at the blood sample carrier site.

In another feature of the disclosure, the group of reliability protocols further includes the power supply module cooperating with the connected measurement engine module and the user interface module to communicate a fault condition message to the user when power supply module resources are insufficient to reliably produce blood test data.

In another feature of the disclosure, the collection modules further include at least one communication module adapted to provide connectivity between the blood glucose test instrument and a separate therapy system. The handheld blood glucose test instrument is further assembled by the interconnection to the interconnection platform of the at least one communication module.

In another feature of the disclosure, the group of reliability protocols further includes the power supply module cooperating with the communication module and the user interface module to communicate a fault condition message to the user interface module when power supply module resources are insufficient to reliably communicate with a separate therapy system.

In another feature of the disclosure, the plurality of different measurement engine modules includes a first measurement engine module that performs electrochemical sensing and a second measurement engine module that performs optical sensing.

In another aspect of the disclosure, a blood glucose test instrument kit having modular component parts capable of being assembled into a plurality of different handheld blood glucose test instruments has been described. The kit includes the combination of an interconnection platform adapted to fit within a portable housing that supports at least one display device and a collection of interoperable modules. Each of the modules having an interface adapted for connection to the interconnection platform. The collection of interoperable modules include a plurality of different measurement engine modules each having an input port to receive a blood sample carrier and producing blood test data, at least one user interface module adapted to couple to the display device and containing test logic for implementing at least one blood glucose test protocol, at least one power supply module adapted, when connected to the interconnection platform, to provide operating power to other modules that are connected to the interconnection platform, at least one communication module adapted to provide connectivity between the blood glucose test instrument and a separate therapy system, and at least one data management module for storing data based upon the blood test data. A handheld blood glucose test instrument is assembled by the interconnection to the interconnection platform of at least one measurement engine module, at least one user interface module, at least one power supply module, at least one communication module and at least one data management module. The interconnection platform providing inter-module communication among the modules connected thereto to achieve enhanced glucose test instrument reliability by effecting at least one reliability protocol selected from the group consisting of (a) a connected measurement engine module from the plurality of measurement engine modules cooperating with a user interface module to instruct the user to remove the blood sample carrier when the measurement engine module detects the blood sample carrier is damaged; (b) the connected measurement engine module cooperating with the user interface module to instruct the user to insert a new code key, when the measurement engine module detects that a previously entered code key is incorrect; and (c) the connected measurement engine module cooperating with the user interface module to instruct the user to repeat an attempted blood glucose test when the connected measurement engine module detects that an insufficient amount of blood or control solution has been deposited was deposited on blood sample carrier.

In another feature of the disclosure, the group of reliability protocols further includes the connected measurement engine module cooperating with the user interface module to instruct the user to repeat an attempted blood glucose test when the connected measurement engine module detects that the user failed to adhere to a sequence defined in the blood glucose test protocol.

In another feature of the disclosure, the group of reliability protocols further includes the connected measurement engine module cooperating with the user interface module to instruct the user to repeat an attempted blood glucose test when the connected measurement engine module detects that an ambient temperature outside of the connected measurement engine module is not within a predefined temperature.

In another feature of the disclosure, the group of reliability protocols further includes the user interface module cooperating with the connected measurement engine module and the data management module to suppress generation of blood test data when an expiry date of a reagent used in the blood sample carrier has been passed and to communicate a fault condition message to the user.

In another feature of the disclosure, group of reliability protocols further includes the user interface module cooperating with the data management module and the measurement engine module to suppress the storing of data based upon the blood test data when the measurement engine module detects a fault condition at the blood sample carrier site.

In another feature of the disclosure, the group of reliability protocols further includes the power supply module cooperating with the connected measurement engine module and the user interface module to communicate a fault condition message to the user when power supply module resources are insufficient to reliably produce blood test data.

In another feature of the disclosure, the group of reliability protocols further includes the power supply module cooperating with the communication module and the user interface module to communicate a fault condition message to the user interface module when power supply module resources are insufficient to reliably communicate with a separate therapy system.

In another feature of the disclosure, the plurality of different measurement engine modules includes a first measurement engine module that performs electrochemical sensing and a second measurement engine module that performs optical sensing.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A blood glucose test instrument kit having modular component parts capable of being assembled into a plurality of different handheld blood glucose test instruments, the kit comprising the combination of:
   an interconnection platform adapted to fit within a portable housing that supports at least one display device;
   a collection of interoperable modules, each of the modules having an interface adapted for connection to the interconnection platform, the collection of interoperable modules including:
   a plurality of different measurement engine modules each having an input port to receive a blood sample carrier and producing blood test data;
   at least one user interface module adapted to couple to said display device and containing test logic for implementing at least one blood glucose test protocol;
   at least one power supply module adapted, when connected to said interconnection platform, to provide operating power to other modules that are connected to said interconnection platform;
   wherein a handheld blood glucose test instrument is assembled by the interconnection to the interconnection platform of at least one measurement engine module, at least one user interface module, and at least one power supply module;
   the interconnection platform providing inter-module communication among the modules connected thereto to achieve enhanced glucose test instrument reliability by effecting at least one reliability protocol selected from the group consisting of:
   (a) a connected measurement engine module from the plurality of measurement engine modules cooperating with a user interface module to instruct the user to remove the blood sample carrier when the measurement engine module detects the blood sample carrier is damaged;
   (b) the connected measurement engine module cooperating with the user interface module to instruct the user to insert a new code key, when the measurement engine module detects that a previously entered code key is incorrect; and
   (c) the connected measurement engine module cooperating with the user interface module to instruct the user to repeat an attempted blood glucose test when the connected measurement engine module detects that an insufficient amount of blood or control solution has been deposited was deposited on blood sample carrier.

2. The blood glucose test instrument kit of claim 1, wherein the group of reliability protocols further comprises the connected measurement engine module cooperating with the user interface module to instruct the user to repeat an attempted blood glucose test when the connected measurement engine module detects that the user failed to adhere to a sequence defined in the blood glucose test protocol.

3. The blood glucose test instrument kit of claim 1, wherein the group of reliability protocols further comprises the connected measurement engine module cooperating with the user interface module to instruct the user to repeat an attempted blood glucose test when the connected measurement engine module detects that an ambient temperature outside of the connected measurement engine module is not within a predefined temperature.

4. The blood glucose test instrument kit of claim 1, wherein the collection of modules further include at least one data management module for storing data based upon said blood test data, and wherein the handheld blood glucose test instrument is further assembled by the interconnection to the interconnection platform of the data management module.

5. The blood glucose test instrument kit of claim 4, wherein the group of reliability protocols further comprises the user interface module cooperating with the connected measurement engine module and the data management module to suppress generation of blood test data when an expiry date of a reagent used in the blood sample carrier has been passed and to communicate a fault condition message to the user.

6. The blood glucose test instrument kit of claim 4, wherein the group of reliability protocols further comprises the user interface module cooperating with the data management module and the measurement engine module to suppress the storing of data based upon said blood test data when the measurement engine module detects a fault condition at the blood sample carrier site.

7. The blood glucose test instrument kit of claim 1, wherein the group of reliability protocols further comprises the power supply module cooperating with the connected measurement engine module and the user interface module to communicate a fault condition message to the user when power supply module resources are insufficient to reliably produce blood test data.

8. The blood glucose test instrument kit of claim 1, wherein the collection of modules further include at least one communication module adapted to provide connectivity between the blood glucose test instrument and a separate therapy system, and wherein the handheld blood glucose test instrument is further assembled by the interconnection to the interconnection platform of the at least one communication module.

9. The blood glucose test instrument kit of claim 8, wherein the group of reliability protocols further comprises the power supply module cooperating with the communication module and the user interface module to communicate a fault condition message to the user interface module when power supply module resources are insufficient to reliably communicate with a separate therapy system.

10. The blood glucose test instrument kit of claim 1, wherein the plurality of different measurement engine modules includes a first measurement engine module that performs electrochemical sensing and a second measurement engine module that performs optical sensing.

11. A blood glucose test instrument kit having modular component parts capable of being assembled into a plurality of different handheld blood glucose test instruments, the kit comprising the combination of:
an interconnection platform adapted to fit within a portable housing that supports at least one display device;
a collection of interoperable modules, each of the modules having an interface adapted for connection to the interconnection platform, the collection of interoperable modules including:
a plurality of different measurement engine modules each having an input port to receive a blood sample carrier and producing blood test data;
at least one user interface module adapted to couple to said display device and containing test logic for implementing at least one blood glucose test protocol;
at least one power supply module adapted, when connected to said interconnection platform, to provide operating power to other modules that are connected to said interconnection platform;
at least one communication module adapted to provide connectivity between the blood glucose test instrument and a separate therapy system; and
at least one data management module adapted to store data based upon said blood test data;
wherein a handheld blood glucose test instrument is assembled by the interconnection to the interconnection platform of at least one measurement engine module, at least one user interface module, at least one power supply module, at least one communication module and at least one data management module;
the interconnection platform providing inter-module communication among the modules connected thereto to achieve enhanced glucose test instrument reliability by effecting a group of reliability protocols, the group of reliability protocols including:
(a) a connected measurement engine module from the plurality of measurement engine modules cooperating with a user interface module to instruct the user to remove the blood sample carrier when the measurement engine module detects the blood sample carrier is damaged;
(b) the connected measurement engine module cooperating with the user interface module to instruct the user to insert a new code key, when the measurement engine module detects that a previously entered code key is incorrect; and
(c) the connected measurement engine module cooperating with the user interface module to instruct the user to repeat an attempted blood glucose test when the connected measurement engine module detects that an insufficient amount of blood or control solution has been deposited was deposited on blood sample carrier;
(d) the connected measurement engine module cooperating with the user interface module to instruct the user to repeat an attempted blood glucose test when the connected measurement engine module detects that the user failed to adhere to a sequence defined in the blood glucose test protocol;
(e) the connected measurement engine module cooperating with the user interface module to instruct the user to repeat an attempted blood glucose test when the connected measurement engine module detects that an ambient temperature outside of the connected measurement engine module is not within a predefined temperature;
(f) the user interface module cooperating with the connected measurement engine module and the data management module to suppress generation of blood test data when an expiry date of a reagent used in the blood sample carrier has been passed and to communicate a fault condition message to the user;
(g) the user interface module cooperating with the data management module and the measurement engine module to suppress the storing of data based upon said blood test data when the measurement engine module detects a fault condition at the blood sample carrier site; and (h) the power supply module cooperating with the connected measurement engine module and the user interface module to communicate a fault condition message to the user when power supply module resources are insufficient to reliably produce blood test data.

12. The blood glucose test instrument kit of claim 11, wherein the group of reliability protocols further comprises the power supply module cooperating with the communication module and the user interface module to communicate a fault condition message to the user interface module when power supply module resources are insufficient to reliably communicate with a separate therapy system.

13. The blood glucose test instrument kit of claim 11, wherein the plurality of different measurement engine modules includes a first measurement engine module that performs electrochemical sensing and a second measurement engine module that performs optical sensing.

* * * * *

UNITED STATES PATENT AND TRADEMARK OFFICE
CERTIFICATE OF CORRECTION

PATENT NO. : 8,383,056 B2
APPLICATION NO. : 12/905485
DATED : February 26, 2013
INVENTOR(S) : Ramey et al.

It is certified that error appears in the above-identified patent and that said Letters Patent is hereby corrected as shown below:

In the Specification

Column 3, line 16, after "detects", insert --that--.

Column 7, line 12, "540," should be --542,--.

Column 8, line 7, "558" should be --560--.

Column 8, line 8, "552." should be --566.--.

Column 8, line 20, before "at", delete "connect to".

Column 8, line 46, before "502-C,", insert --502-B,--.

Column 9, line 23, "210" should be --610--.

Column 9, line 50, "630." should be --620.--.

Column 11, line 4, before "read", insert --to--.

Column 12, line 34, after "not", delete "be".

Column 12, line 50, after "detects", insert --that--.

Column 13, line 57, "6 C" should be --6°C--.

Column 13, line 58, "44 C," should be --44°C,--.

Column 13, line 61, "command" should be --commands--.

Column 14, line 42, "1310" should be --1410--.

Column 14, line 43, "1300" should be --1400--.

Signed and Sealed this
Seventeenth Day of June, 2014

Michelle K. Lee
*Deputy Director of the United States Patent and Trademark Office*

CERTIFICATE OF CORRECTION (continued)
U.S. Pat. No. 8,383,056 B2

Column 14, line 63, "1310" should be --1510--.

Column 14, line 63, "1300" should be --1500--.

Column 15, line 23, after "of", insert --:--.

Column 15, line 27, after "detects", insert --that--.

Column 15, line 36, after "solution", delete "has been deposited".

Column 16, line 59, after "of", insert --:--.

Column 16, line 63, after "detects", insert --that--.

Column 17, line 5, after "solution", delete "has been deposited".

In the Claims

Column 18, line 62, after "solution", delete "has been deposited".

Column 20, line 42, after "solution", delete "has been deposited".